United States Patent [19]

Dickerson

[11] Patent Number: 5,365,068
[45] Date of Patent: Nov. 15, 1994

[54] SUN PROTECTION CALCULATOR AND TIMER

[76] Inventor: William H. Dickerson, 237 N. Marlyn Ave., Baltimore, Md. 21221

[21] Appl. No.: 141,224
[22] Filed: Oct. 26, 1993
[51] Int. Cl.[5] .............................. G01J 1/00; G01J 1/42
[52] U.S. Cl. ...................... 250/372; 340/600
[58] Field of Search ............. 250/372 EM, 372; 340/600; 128/653.1

[56] References Cited

U.S. PATENT DOCUMENTS

| | | | |
|---|---|---|---|
| 4,749,865 | 6/1988 | Schelbr | 250/372 EM |
| 4,818,491 | 4/1989 | Tariff | 250/372 EM |
| 5,036,311 | 7/1991 | Moran et al. | 340/600 |

*Primary Examiner*—Paul M. Dzierzynski
*Assistant Examiner*—Richard Hanig
*Attorney, Agent, or Firm*—Terrance L. Siemens

[57] ABSTRACT

A portable device for calculating the optimal safe sun protection factor (SPF) lotion to be applied by the user under local ambient conditions. The user inputs their skin type (fair, medium, or dark), and the amount of time they wish to spend in the sun. The apparatus then calculates a corresponding SPF number when the ultraviolet (UV) radiation sensing means is exposed to the existing impinging light conditions. A timer is set which allows the user to be notified when the predetermined amount of exposure time has been reached. The device includes a photovoltaic (PV) cell for self power having a battery back-up if ambient light conditions, and thus the generated photovoltaic output, falls beneath a predetermined threshold.

7 Claims, 4 Drawing Sheets

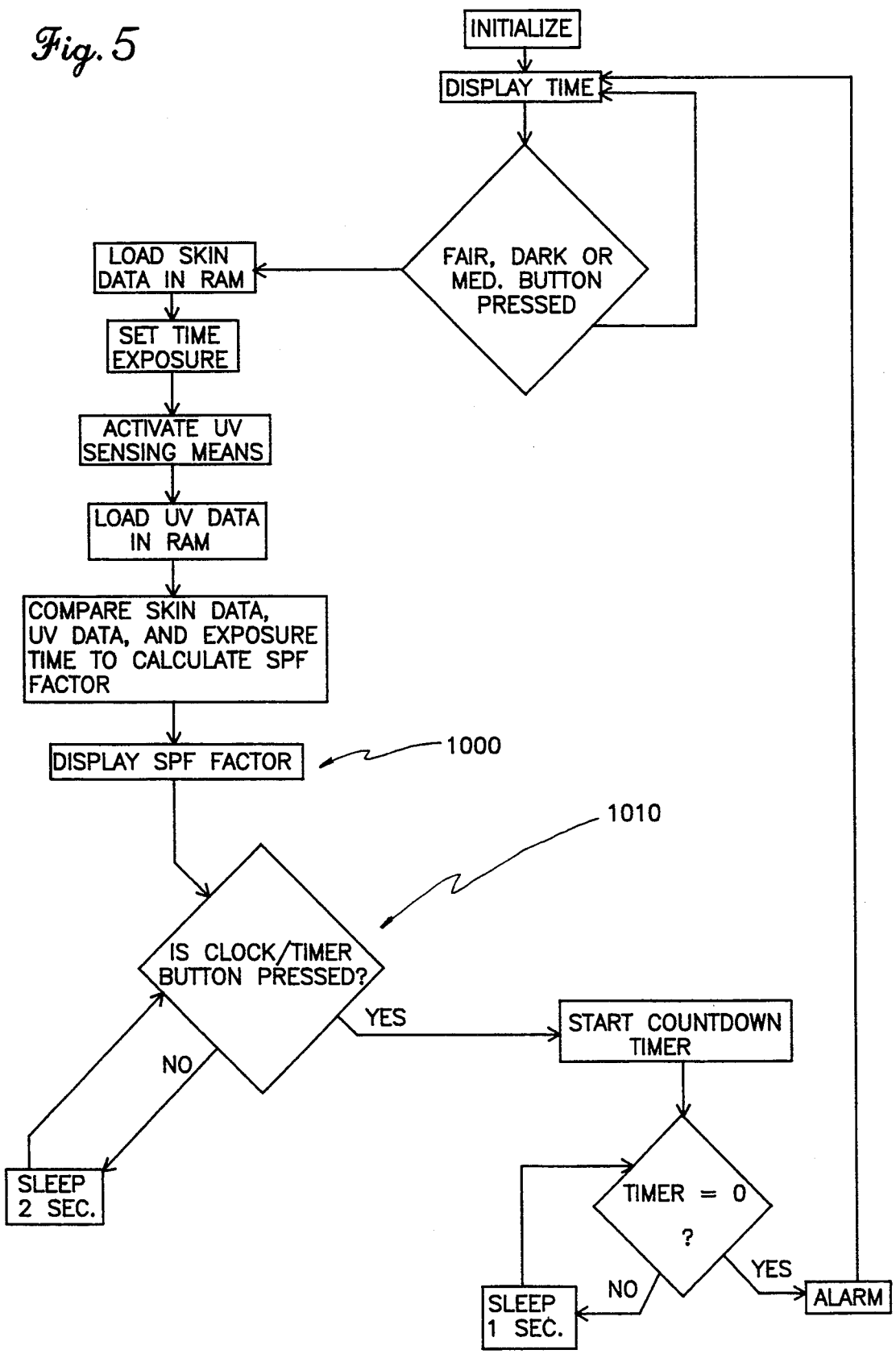

SUN PROTECTION CALCULATOR AND TIMER

BACKGROUND OF THE INVENTION

1. Field of the Invention

The present invention relates to protection of human skin from harmful ultraviolet light. More specifically, it relates to a device that measures the amount of ultraviolet (UV) radiation impinging on a detector, compares it with a predetermined or indicated skin type and desired exposure time, and displays a sun protection factor (SPF) that is appropriate for both of these conditions. The SPF is commonly displayed on commercially available "sunblock" tanning lotions. With this invention the user will know the appropriate strength lotion to purchase for a particular day at the beach or, if several strengths have already been purchased, which one is appropriate for that day. The "appropriate" lotion may be either one which will allow maximal tanning in minimal time without risk of sunburn damage to the skin or one which will safely block the majority of the sun's harmful radiations. Of course the determination of what is appropriate is a matter for individual user decision. This invention simply provides the user with the necessary data to make that decision wisely.

It is also contemplated that the field of this invention could extend beyond the protection of humans from harmful rays from the sun. It is well known that portions of the sun's spectrum are harmful to many physical items which must be located outdoors. Some common examples are exterior paint on houses and buildings, automotive finishes, and automotive tires. Simple alteration of the sensing and comparison logic tables of this invention would provide researchers with a valuable tool for assessing and testing various protective coatings for use outdoors.

Thus it can be seen that the potential fields of use for this invention are myriad and the particular preferred embodiment described herein is in no way meant to be limiting the particular field chosen for exposition of the details of the invention.

2. DESCRIPTION OF THE PRIOR ART

People, in the course of work or recreation, spend a great deal of time outdoors. As much as the society has become more technologically advanced and oriented towards working indoors, some of us must still make our living in the outdoors, with all the attendant hazards that go along. Even for those people whose work is all, or mostly all, done indoors, outdoor sports such as walking, cycling, and the like are popular on the weekends or in their off-time hours. A hazard that is easily preventable in these activities is sunburn, or erythema, the known skin response to exposure to UV rays in the range of 250–400 nanometers. Not only is this response painful, but it is also damaging to the skin, drying it out and potentially leading to skin cancers of various types if the skin is exposed consistently over years of cosmetic "sunbathing". It is possible, in cases of extreme overexposure, to cause third-degree burns of a very serious medical nature.

As these dangers have become more widely known, the use of "sunblocks" has become more common. These are generally creams or lotions having within them a substance that blocks or absorbs the UV rays in the dangerous region of the overall electromagnetic spectrum of sunlight. These lotions are rated on an SPF (sun protection factor) scale, from 1 up to 60, and even higher. A problem that arises, especially for someone who wishes to tan for cosmetic reasons is that if a block is used with too high a SPF, their time in the sun, which may be limited due to work or other constraints, can be wasted, showing no results, or a result which they consider disappointing. The other side of the coin is that if the SPF used is too low, a painful burn or even more serious medical consequences can ensue. Currently, people are put in the position where they have to simply guess what the proper factor is to use on a given day and over a set time. The present invention attempts to overcome this problem by providing an output of a proper SPF for given conditions while taking into account the user's skin type and the amount of time that the user wishes to spend in the sun. There are a number of U.S. Patents issued that bear on this matter.

In U.S. Patent No. 4,428,050 issued on Jan. 24, 1984 to Frank Pellegrino et al. there is disclosed a tanning aid wherein a number of factors are entered into the device such as initial skin type, the SPF factor to used, the desired skin pigmentation, and the number and duration of sessions to be used to achieve the desired result. The device then sounds appropriate alarms when the determined intervals are reached according to the sun conditions sensed by an optical detector with a UV filter. The SPF must be entered into this device in order for it to function meaningfully. Contrast this with applicants invention where the output is an SPF factor appropriate to the conditions, the indicated skin type, and the time the user wishes to sunbathe.

Next is U.S. Pat. No. 4,962,910 issued on Oct. 16, 1990 to Atsuko Shimizu. In this patent, a device for use to prevent human skin from excessive sunburn is disclosed. Skin type data and an SPF factor are input and critical values for UV radiation exposure are calculated. Alarm sounds are activated when these critical values are reached compared to measured radiation dosages over a predetermined time. As in Pellegrino et al. above, the SPF factor must be input by the user.

In U.S. Pat. No. 4,985,632 issued on Jan. 15, 1991 to Frank J. Bianco et al. there is disclosed a suntan indicator. In this device, as in Shimizu and Pellegrino et al., the SPF factor used is input along with the skin type and the remaining time to remain exposed to the sun is displayed.

U.S. Pat. No. 5,008,548 issued on Apr. 16, 1991 to Nahum Gat discloses a personal UV radiometer. It includes a photocell and filter to measure the amount of ambient UV radiation, a bar graph or other indication means to display the strength of the radiation, and a numeric display that can output time remaining or percent of desired exposure to a predetermined energy intensity per unit area in millijoules per square centimeter, $mJ/cm^2$. As in the above discussed patents, an SPF factor is input manually into the device.

Lastly, U.S. Pat. No. 5,036,311 issued on Jul. 30, 1991 to Dan Moran et al. discloses a UV exposure monitoring system wherein skin color and SPF factor are input into the device and an alarm is activated when the user reaches a point of time where they are in danger of developing an erythemal reaction.

All of the above mentioned prior patents require that the user know in advance what SPF lotion they will be using. The presumption is made that the user has already purchased their lotion and are ready for their day at the beach. The instant invention makes no such presumptions. The user of the instant invention is at the beach, perhaps for a limited amount of time, and will be informed of the SPF lotion to be used to safely optimize the cosmetic tanning of their skin in their time on their day. Thus, for example, the instant invention is capable of being used in combination with a vending machine on the beach for dispensing the appropriate single use SPF lotion to individual users. The prior patents in this field did not contemplate such a use and are incapable of performing in such a context.

None of the above inventions and patents representing the prior art, taken either singly or in combination, anticipates or makes obvious the invention claimed herein.

SUMMARY OF THE INVENTION

The preferred embodiment of this invention provides a portable device for calculating the necessary SPF lotion to be applied by the user under local ambient conditions. The user first must enter their skin type (fair, medium, or dark), and the amount of time that they wish to spend in the sun under those conditions. The apparatus then calculates a corresponding SPF number when an included UV radiation sensing means is exposed to the existing conditions. A timer is set which allows the user to be notified when the predetermined amount of exposure time has been reached. The device includes a photovoltaic (PV) cell for self power having a battery backup if ambient light conditions, and thus the generated photovoltaic output, fall beneath a predetermined threshold.

Accordingly, it is a principal object of the invention to provide a sun protection calculator that displays an SPF (sun protection factor) value appropriate for an predetermined skin type when exposed to ambient local conditions.

It is another object of the invention to provide a sun protection calculator having a timer disposed therein for activating an alarm when a predetermined amount of time has passed.

It is a further object of the invention to provide a sun protection calculator wherein the displayed SPF number will provide for maximum UV protection and maximum tanning for the ambient local conditions to which it is exposed.

Still another object of the invention is to provide a sun protection calculator that is powered by solar energy and further contains a back-up battery power means that is activated when the photovoltaic current falls below a predetermined threshold.

A general goal is to provide improved elements and arrangements thereof in an apparatus for the purposes described which is inexpensive, dependable, and fully effective in accomplishing its intended purposes.

It is submitted that the present invention meets or exceeds all the above objects and goals. Upon further study of the specification and appended claims, further objects and advantages of this invention will become apparent to those skilled in the art.

These and other objects of the present invention will become readily apparent upon further review of the following specification and drawings.

BRIEF DESCRIPTION OF THE DRAWINGS

Various other objects, features, and attendant advantages of the present invention will become more fully appreciated as the same becomes better understood when considered in conjunction with the accompanying drawings, in which like reference characters designate the same or similar parts throughout the several views, and wherein:

FIG. 5 is a flow chart showing the logical steps taken in the operation of the invention.

DETAILED DESCRIPTION OF THE PREFERRED EMBODIMENT

Figure 1:
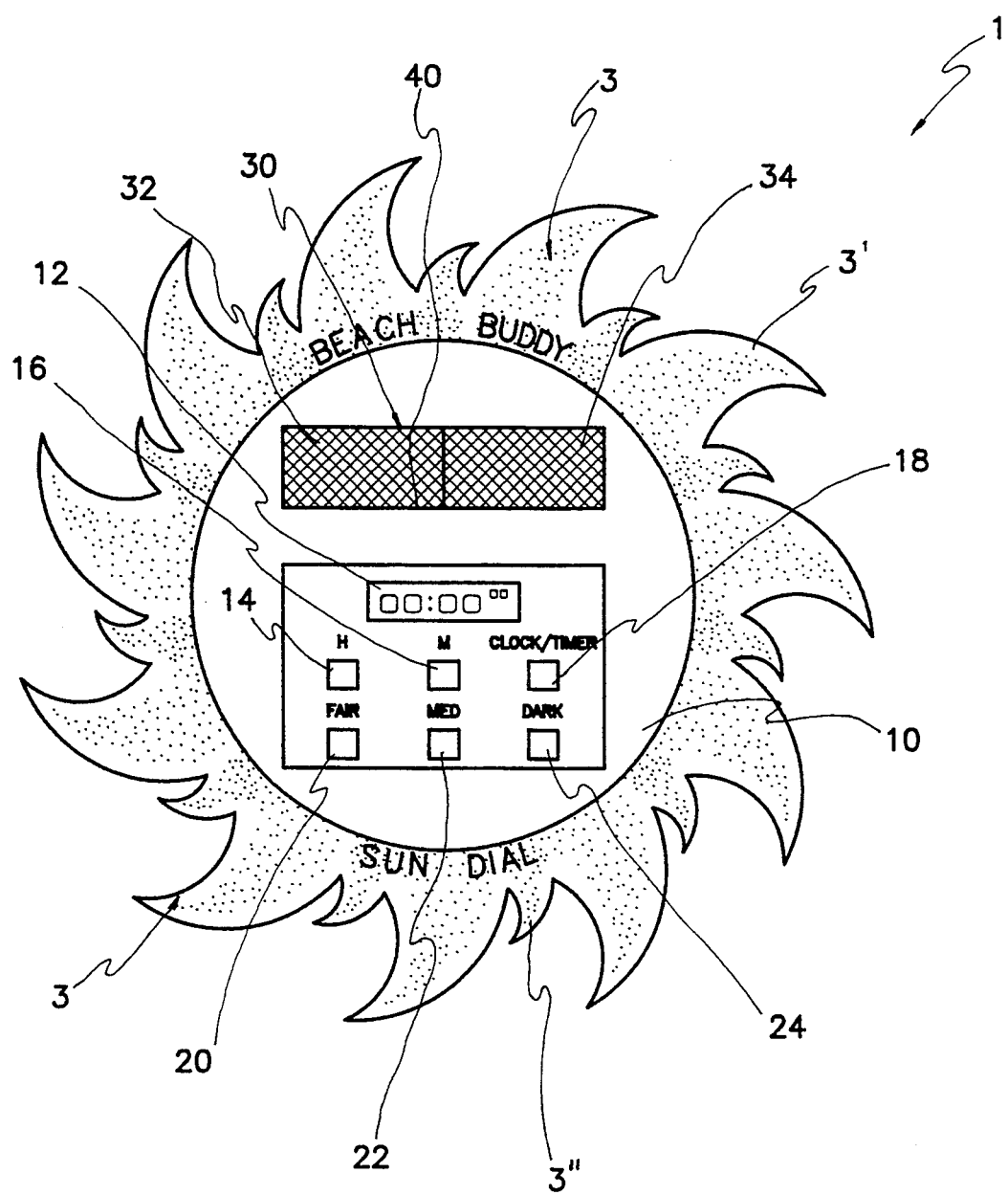
FIG. 1 is a top view looking directly at the front outside face of the present invention.
Figure 2:
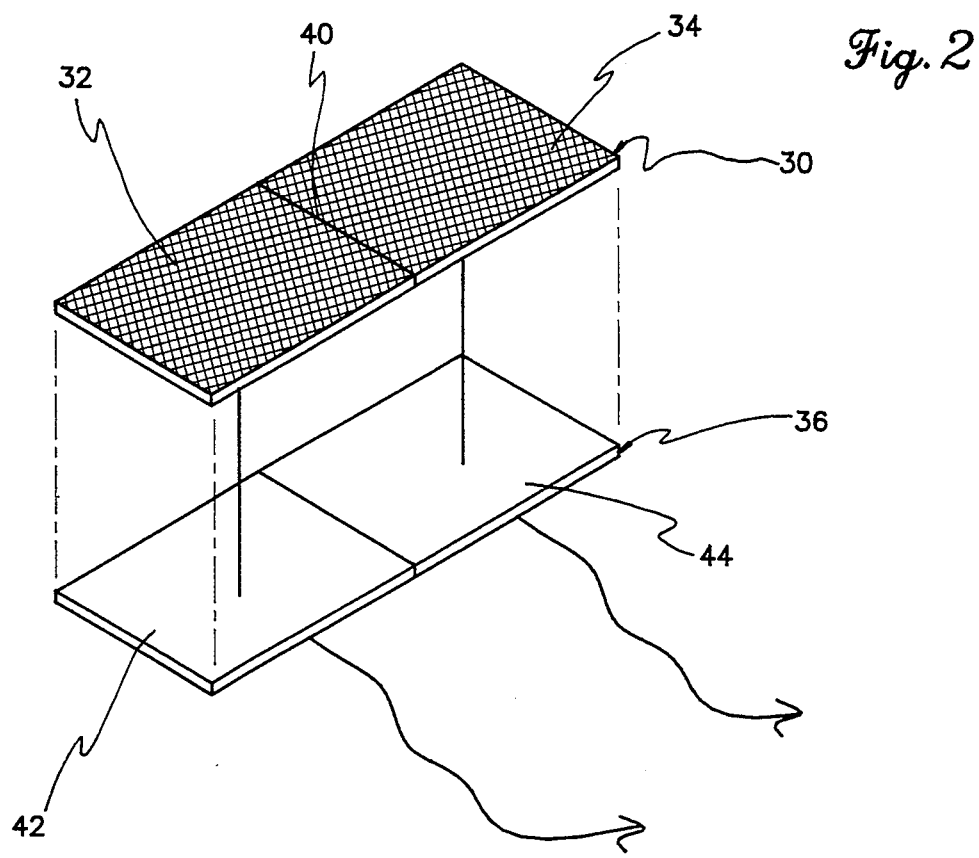
FIG. 2 is an exploded view of the dual PV (photovoltaic) cell array and the dual light transmissive cover and filter that allow for both powering the apparatus and sensing the ambient UV radiation in the local environment.

Referring to FIG. 1, the present invention is shown in a preferred embodiment and is generally indicated at 1. In overall appearance, the apparatus 1 is a fanciful representation of the sun. It has an encircling outer portion 3 that represents the suns rays that includes a number of alternatingly sized, generally outwardly extending portions 3' and 3''. Centrally disposed in the device is a front input and display panel 10 and, on the opposite side from panel 10, is a back portion 11 which is best seen in FIG. 2. Though size is not critical to the operation of the device, it is contemplated that it should be of sufficient size so that the displays can be easily read and the buttons or switches (as will be discussed hereinafter) can be manipulated without difficulty. It should also be noted, however, that the device should not be so large that it would be clumsy or unwieldy to carry. The outer shell of the apparatus 1 could be made of a number of materials, but a high impact plastic of waterproof construction would be inexpensive to manufacture and would aid in obviating accidental breakage.

In FIG. 1, on the front panel 10 there is disposed an alphanumeric display area 12, an hour set button 14, a minute set button 16, and a clock/timer toggle button 18. Below these, when the device is held normally, are the skin type selection buttons. These comprise a fair skin selector 20, a medium skin selector 22, and a dark skin selector 24. The use of these will be discussed in more detail below.

Figure 3:
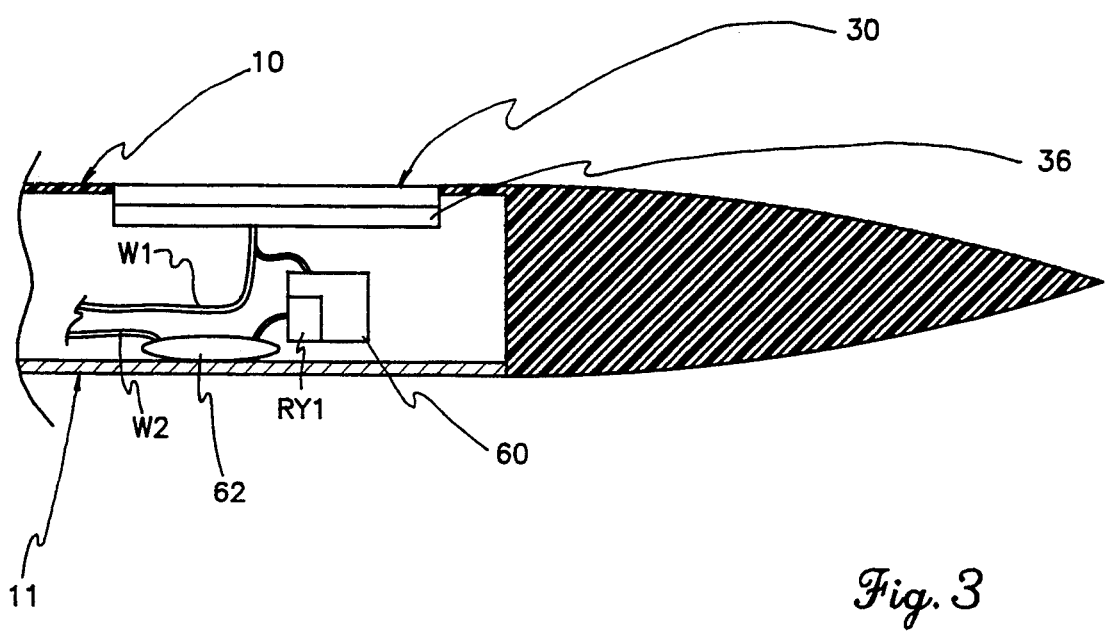
FIG. 3 is a representational side cutaway view of the device showing the dual PV (photovoltaic) array, the backup battery, and a representation of the voltage sensing means that activates the backup battery at a predetermined power level.

Referring now to FIGS. 1, 2, and 3, the UV sensing means and the photovoltaic power means will be discussed. Flush with the front panel 10 is a combination light transmissive cover and filter 30. The first part of the cover/filter is cover portion 32 and filter portion 34, both seen in FIGS. 1 and 2. Beneath these, as seen in FIG. 2 is a dual PV (photovoltaic) cell array 36. This is divided medially into two sections 42, 44 approximately as shown in FIG. 2. Each of the sections is separate, with section 42 being the principal power source for the device, and section 44 serving as the UV detection means. The filter portion 34 disposed above photovoltaic section 44 is adapted to only pass the dangerous burning UV rays that lie in the wavelength range of 250–400 nanometers. Thus the current produced from PV section 44 will be dependent on the UV radiation level within the range that is known to be the most dangerous to human skin. The other PV section 42 has no filter over it, thereby allowing it to function as an efficient solar power source for the apparatus. In the event that the ambient light is insufficient for the demands of the apparatus, a current monitor 60 is placed along wire W1 such that if the current being produced by PV section 42 drops below a certain limit, switch relay RY1 is thrown, allowing current to flow into the device from the backup battery 62 along wire W2, as is seen in FIG. 3.

Figure 4:
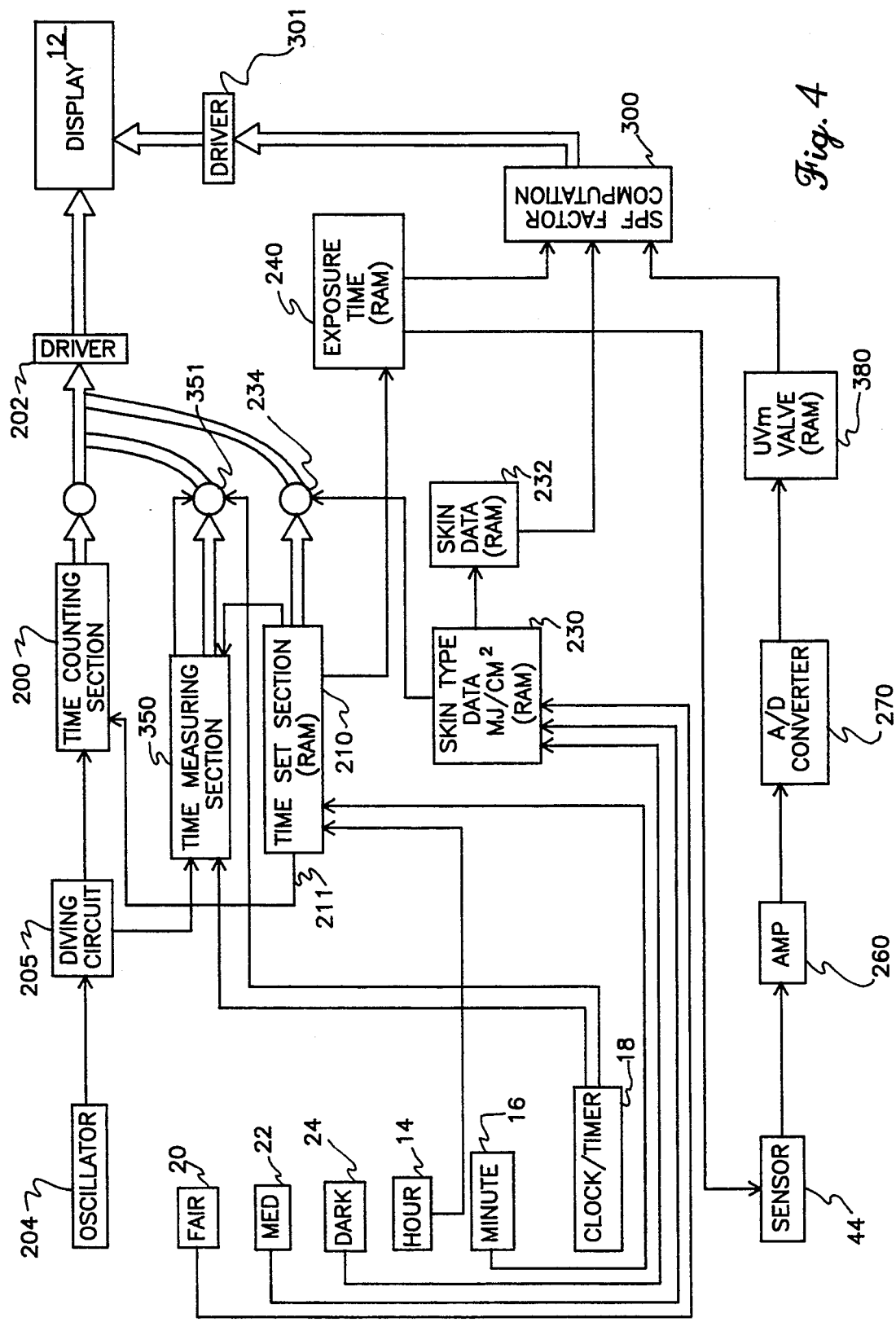
FIG. 4 is a block diagram illustrating part of the circuit arrangement in the present invention.

The discussion now turns to FIGS. 4 and 5 and the way in which the device operates and functions; however first some further explanation is necessary to clarify the terms that will be used below. Human skin type has been classified in regard to how much melanin pigmentation it contains, this, of course, being an indication of how much harmful ultraviolet radiation it can be subjected to before an erythemal reaction occurs. These skin types are listed as follows in Table 1 adapted from the prior art Shimizu patent discussed above:

TABLE 1

| SKIN TYPE | DESCRIPTION-BURN RISK & TANNING ABILITY |
|---|---|
| 1 | Fair skin. Burns easily. Never tans. |
| 2 | Fair skin. Burns easily. Minimal tan. |
| 3 | Light brown skin. Burns moderately. Tans gradually. |
| 4 | Moderate brown skin. Burns minimally. Always tans well. |
| 5 | Dark brown skin. Rarely burns. Tans profusely. |
| 6 | Dark brown skin. Never burns. Deeply pigmented |

As the skin type number grows larger, the amount of ultraviolet radiation it can tolerate before being damaged grows larger as can be seen from the following table 2, which is taken from the prior art Bianco et al. patent discussed above:

TABLE 2

| SKIN TYPE | UV DOSAGE (mJ/cm$^2$) |
|---|---|
| 1 | 15,000 |
| 2 | 25,000 |
| 3 | 30,000 |
| 4 | 45,000 |
| 5 | 60,000 |
| 6 | 99,000 |

The figures in the above two Tables should be taken as representational, as they relate only to UV type B radiation. However, they adequately serve to demonstrate that a distinct relationship exists between these existing skin type classifications and the of UV radiation energy per square centimeter of exposed skin (mJ/cm$^2$) that can be absorbed before damage occurs.

The first step for use of the device would be the initialization process, which would entail setting the correct time into the time set section 210 of RAM (random access memory) through the hour set button 14 and the minute set button 16. The time set section 210 would then pass it on as shown by arrow 211 to the time counting section 200. The time counting section then passes it on to the driver 202, and through well known means of a conventional oscillator 204, would thus increment the display 12. Thus the device 1 is functional as a decorative watch or simple timepiece at this point and could be carried about the neck on a chain or the like.

The routinist will recognize that the protruding fanciful representations of sun rays about the perimeter of the device could be eliminated or covered with an disk shaped carrying case similar to a pocket watch to facilitate the portability of the device in a purse, wallet, or pocket.

When it is desired to use the apparatus 1 in its capacity as a sun protection calculator, the user chooses which of the buttons 20, 22, or 24 best describe their skin type. It would, of course, be mentioned in the instructions that came with the apparatus, that it would be smarter to guess on the safe side: i.e. to press "fair" if you're not sure whether you qualify as "medium" or not. It is assumed that most people have the experience to judge which category they fit into.

The selection of one of the skin type buttons 20, 22, 24 reads skin type data regarding the mJ/cm$^2$ of UV radiation that type of skin can be subjected to before sustaining damage out of a skin data portion of ROM (read only memory) in the apparatus and transfers it to a skin data portion of RAM 232. Referring above to table 2, for example, the "fair" button would correspond to skin types 1 and 2 and would transfer a value of 18,000. The value transferred would preferably be significantly less than the average of the values as shown in table 2, to allow for the wide range of skin types that are present. The "medium" button, for example, could transfer a value of 33,300; and the "dark button could transfer 71,550 as its maximum mJ/cm$^2$ value permitted. This represents the average of these example values as seen in table 2 with ten percent deducted. More or less could be deducted, depending on the manufacturer's or the users wishes, by reprogramming the apparatus. A slider (not shown) for example, could be mounted in the interior of the unit to weight this average in any manner desired. As the skin type data in ROM at 230 is sent to the RAM skin data 232 an additional signal is sent to a gate circuit 234 that transfers the data from the time set section 210 to the driver 202 and thus to the display 12. The user now enters in the exposure time using the hour set button 14 and the minute set button 16. This information is displayed through the driver 202 onto the display 12 and also is sent to the exposure time address in RAM 240. As this takes place, a signal is sent to the UV sensor 44, which is activated for a predetermined period of time. It is contemplated that this period should be at least fifteen seconds, and probably closer to forty five as this would allow the user to make sure that the UV sensing portion 44 was pointed in the proper direction to acquire an accurate light intensity reading. The voltage produced by the UV sensor 44 is outputted to the amplifier 260, then sent to an analog to digital (A/D) converter 270, and finally is digitally stored in the UV$_m$ value RAM 280. The SPF factor computation unit 300, which could be any of a known variety of microprocessors, then relates the data in the UV$_m$ value RAM 280, the skin data RAM 232, and the exposure time RAM 240 according to the following equation:

$$\text{SPF factor} = \left( \frac{\text{exposure time}}{\text{mJ/cm}^2} \right) * UV_m$$

The result of this equation is then sent to driver 301 and thence to display 12.

Turning now to FIG. 5, you can see specifically at the step in the flowchart indicated at 1000 that it is at this point wherein the SPF factor, having been calculated, is being displayed. It should be understood that the following is only a single way of accomplishing the next step in the functioning of the instant invention. In the step labeled 1010, an interrogation is made within the time measuring section 350 to the gate circuit 351 (both seen in FIG. 4) see whether or not the clock-/timer toggle switch 18 has been pressed. If not, the device waits two seconds and then interrogates again. When the toggle 18 has been pressed, the gate circuit 351 passes the output of the time measuring section 350, as fed by the oscillator 204 through the dividing circuit 205 to the driver 202, and thus to the display 12. As a consequence a countdown timer is activated so as to activate an alarm after a preset time period and return the display to the time of day mode.

From the foregoing description, one skilled in the art can easily ascertain the essential characteristics of this invention and, without departing from the spirit and scope thereof, can make various changes and modifications of the invention to adapt it to various usages and conditions.

It is to be understood that the present invention is not limited to the sole embodiment described above, but encompasses any and all embodiments within the scope of the following claims.

I claim:

1. An apparatus for displaying an optimum safe sun protection factor (SPF) to provide skin protection from harmful sunlight for a user predetermined exposure time in local ambient conditions comprising:
   a body having a peripheral decorative portion and an inner face including input and display portions;
   electrical power means within said body including a photovoltaic cell to provide electrical energy;
   a first changeable setting timekeeping circuit means for local timekeeping;
   a second changeable setting time keeping circuit means to count down said predetermined exposure time;
   first input means for setting both said first and second changeable setting timekeeping circuit means;
   second input means for selecting one of at least three skin types, the skin types being demarcated along skin type susceptibility to ultraviolet radiation;
   ultraviolet sensing means for measuring the ambient ultraviolet radiation intensity (mJ/cm$^2$);
   internal storage means for data pertaining to the maximum energy absorption per unit area (UV$_m$) of ultraviolet radiation that is allowable for each of the skin types selectable by said second input means;
   computation means to calculate said sun protection factor based upon said predetermined exposure time, said skin type input by said second input means, and said internally stored data according to the equation $$\text{SPF factor} = \left( \frac{\text{exposure time}}{\text{mJ/cm}^2} \right) * UV_m$$

sun protection factor (SPF) output display means for indicating said optimum safe sun protection factor (SPF) to the user in the local ambient conditions.

2. The apparatus according to claim 1, wherein said peripheral decorative portion is generally annular and is formed to suggest a fanciful representation of the sun's rays.

3. The apparatus according to claim 1, wherein said first input means is a plurality of pushbuttons.

4. The apparatus according to claim 3, wherein said plurality of pushbuttons include separate buttons for setting the hour and the minute.

5. The apparatus according to claim 1, further including a secondary battery power source which automatically operates when the output from said photovoltaic cell drops below a predetermined level.

6. The apparatus according to claim 5, wherein a light gathering panel for said photovoltaic cell and a light filtering panel of said ultraviolet sensing means are directly adjacent one another on said inner face of said body.

7. The apparatus according to claim 1, wherein said second changeable setting timekeeping circuit means includes an alarm means for alerting the user when said predetermined exposure time has expired.

* * * * *